United States Patent
Ibrahim et al.

(10) Patent No.: US 8,338,347 B2
(45) Date of Patent: Dec. 25, 2012

(54) SYSTEM FOR REDUCING BACTERIA ON UNPROCESSED FOOD SURFACES WHILE EXTENDING SHELF LIFE

(76) Inventors: Mareya Shawki Ibrahim, Aliso Viejo, CA (US); Shawki Amin Ibrahim, Fort Collins, CO (US)

( * ) Notice: Subject to any disclaimer, the term of this patent is extended or adjusted under 35 U.S.C. 154(b) by 0 days.

(21) Appl. No.: 13/020,874

(22) Filed: Feb. 4, 2011

(65) Prior Publication Data

US 2012/0065269 A1 Mar. 15, 2012

Related U.S. Application Data

(60) Provisional application No. 61/381,074, filed on Sep. 9, 2010.

(51) Int. Cl.
*A01K 43/00* (2006.01)
*C11D 3/20* (2006.01)
*C11D 3/37* (2006.01)

(52) U.S. Cl. .................................. 510/111; 510/361

(58) Field of Classification Search .................. None
See application file for complete search history.

(56) References Cited

U.S. PATENT DOCUMENTS

2006/0193954 A1* 8/2006 Pruett et al. .................. 426/335

* cited by examiner

*Primary Examiner* — Sreeni Padmanabhan
*Assistant Examiner* — Layla Soroush
(74) *Attorney, Agent, or Firm* — One LLP

(57) ABSTRACT

A system for substantially reducing surface contaminants of a food substance comprising a substantially transparent and odorless solution made from a plurality of substantially organic compounds selected from: citric acid, sodium citrate, vegetable glycerin, sea salt, potassium sorbate, decyl glucoside, calcium ascorbate, grapefruit seed extract, and sodium bisulfite, and an applicator for applying the solution to the food substance. The solution ratio of organic compounds is approximately: 2% citric acid, 2% sodium citrate, 0.2% vegetable glycerin, 0.2% potassium sorbate; 0% to 0.4% decyl glucoside, 0% to 0.2% calcium ascorbate, 0% to 0.2% grapefruit seed extract, 0% to 0.1% sodium bisulfite, and 0.2% to 2% sea salt.

12 Claims, 1 Drawing Sheet

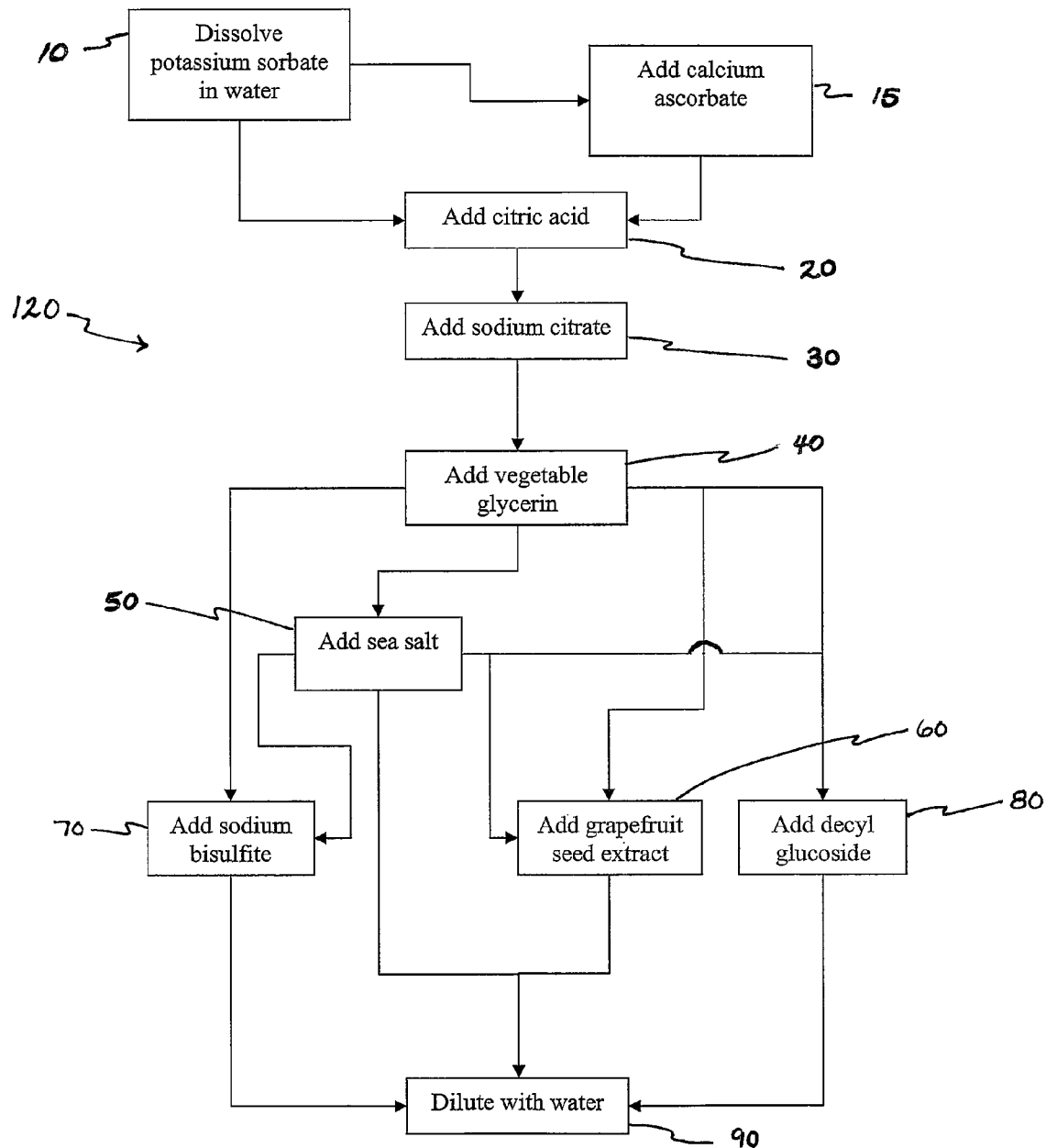

SYSTEM FOR REDUCING BACTERIA ON UNPROCESSED FOOD SURFACES WHILE EXTENDING SHELF LIFE

CROSS-REFERENCE TO RELATED APPLICATIONS

This application is based on and claims the benefit of the filing of U.S. Provisional Patent Application No. 61/381,074 filed Sep. 9, 2010, the contents and disclosure of which is fully incorporated herein by reference.

BACKGROUND OF THE INVENTION

Field of the Present Disclosure

The invention relates to a system of substantially reducing bacteria and contaminants on food surfaces, primarily fresh produce, seafood and poultry, while simultaneously extending shelf life, reducing spoilage, bacteria and mold growth by applying an antimicrobial, antioxidant solution made from all natural compounds to the food surface. The system is applied via a liquid solution or a biodegradable wipe treated with the solution. The wipes do not require rinsing.

Food borne illnesses are an increasing concern in homes across the country. These illnesses are present in part because the foods being sold at grocery stores are grown in organic soil and manure and treated with pesticides and chemicals, then covered with non-water soluble wax, which can make foods dangerous to consumers upon ingestion. Additionally, these illnesses are sometimes spread when food is not washed or stored properly, causing the bacteria, dirt, or other particles naturally found in or on the food to be ingested. While consumers are generally aware of the risks of food borne illnesses, they nonetheless fail to effectively remove the chemicals and bacteria that is the cause.

Waste of fresh produce is one of the leading causes of methane emissions in landfills. According to the U.S. Department of Agriculture, Fresh fruits and vegetables accounted for nearly 20 percent of consumer and foodservice losses. Methane gas from fresh fruit and vegetables is considered 21 times more harmful than carbon dioxide. The environmental impact of this waste affects the global economy.

Most consumers simply wash foods with plain water, however this method generally fails to effectively bring harmful chemicals and bacteria to a safe level for human consumption. Furthermore, water is generally ineffective at removing protective wax from fruits and/or vegetables. Other food wash solutions with chemical compounds are also available. These chemicals are often harsh smelling, turbid, and leave a residue that affects the taste of the food or unsafe if ingested. Solutions are available that are effective in reducing bacteria and pesticide content, and that do not leave a chemical residue; however these washes are generally a disinviting color and are accompanied by a bad taste, both of which discourage usage.

It is therefore desirable for an organic food wash solution that is substantially odorless, colorless, tasteless and safe, and which can be easily produced at low cost and effort.

BRIEF SUMMARY OF THE INVENTION

The primary objective of this invention is to provide an all natural solution that is easily produced without resort to dangerous or artificial chemicals or heat, and which can remove dirt, pesticides, chemicals and odors, and which can reduce oxidation and spoilage of fresh food, without leaving a residual chemical taste or smell.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least one of the best mode embodiments of the present invention In such drawing(s):

FIG. 1 illustrates a preferred order that organic compounds are dissolved according to a preferred embodiment.

DETAILED DESCRIPTION OF THE INVENTION

The above described drawing figures illustrate the described solution and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

A system 100 for substantially reducing surface bacteria of a food substance comprises: a solution 120 of a plurality of substantively organic compounds dissolved in water, and an applicator 110 for applying the solution to the food substance. The solution is substantially transparent, tasteless and odorless. The applicator may be a wipe, towelette, sponge, spray bottle or any other type of applicator operable to apply the solution to a surface of the food substance.

In a preferred embodiment, the solution preferably consists of a plurality of all natural compounds. A first compound is operable to substantially kill bacteria, remove wax, and inhibit browning, and is preferably citric acid. A second compound is operable to substantially increase bacteria kill efficacy and prolong shelf life, and is preferably sodium citrate. A third compound is operable to substantially increase bacteria kill efficacy and prolong shelf life, and is preferably sea salt. A fourth compound is operable to facilitate adherence of the solution to a food surface and is preferably vegetable glycerin. A fifth compound is operable to preserve a substantially transparent color in the solution, and to substantially prevent mold and bacteria growth, and is preferably potassium sorbate. A sixth compound is operable to facilitate the removal of mud, fat soluable contaminants, pesticide residue and the like, and is preferably decyl glucoside or cocamidopropyl hydroxysultaine. A seventh compound is operable to substantially inhibit browning, and is preferably calcium ascorbate.

In a preferred embodiment, the solution preferably consists of a plurality of substantively organic compounds selected from: citric acid, sodium citrate, vegetable glycerin, sea salt, decyl glucoside, cocamidopropyl hydroxysultaine, calcium ascorbate, potassium sorbate, grapefruit seed extract, and sodium bisulfite. The compounds are preferably dissolved in distilled, deionized or triple filtered water.

In a preferred embodiment, the solution comprises approximately: 2% to 4% citric acid, 2% to 4% sodium citrate, 0.2% to 1.4% vegetable glycerin, 0.2% to 0.4% potassium sorbate; 0% to 0.8% decyl glucoside, 0% to 0.2% calcium ascorbate, 0% to 0.2% grapefruit seed extract, 0% to 0.1% sodium bisulfate, and 0.2% to 2% to 4% sea salt. The compounds are preferably dissolved in deionized or triple filtered water to produce the solution.

In one embodiment, the solution consists of: 93.6% water, 2% citric acid, 2% sodium citrate, 2% sea salt, 0.2% vegetable glycerin and 0.2% potassium sorbate. In the system of the present embodiment, the solution is preferably applied to seafood and poultry via a spray applicator. Alternatively, the solution may be applied to fruit and vegetables via towlette applicators.

In an alternative embodiment, the solution consists of: 93.1% water, 2% citric acid, 2% sodium citrate, 2% sea salt, 0.2% vegetable glycerin, 0.2% potassium sorbate, 0.4% decyl glucoside, and 0.1% calcium ascorbate. In the system of the present embodiment, the solution is preferably applied to fruits and vegetables via a spray applicator.

In an alternative embodiment, the solution consists of 87.4% water, 4% citric acid, 4% sodium citrate, 4% sea salt, 0.4% vegetable glycerin and 0.2% potassium sorbate.

In another embodiment, the solution consists of: 86.2% water, 4% citric acid, 4% sodium citrate, 4% sea salt, 0.4% vegetable glycerin, 0.4% potassium sorbate, 0.8% decyl glucoside, and 0.2% calcium ascorbate.

In an alternative embodiment, the solution consists of: 95.2% water, 2% citric acid, 2% sodium citrate, 0.2% sea salt, 0.2% vegetable glycerin, 0.2% potassium sorbate, and 0.2% calcium ascorbate.

In an alternative embodiment, the solution consists of: 95% distilled water, 2% citric acid, 2% sodium citrate, 0.2% sea salt, 0.2% vegetable glycerin, 0.2% potassium sorbate, 0.2% decyl glucoside, and 0.2% calcium ascorbate.

In an alternative embodiment the solution consists of: 95.2% distilled water, 2% citric acid, 2% sodium citrate, 0.2% grapefruit seed extract, 0.2% vegetable glycerin, 0.2% potassium sorbate, and 0.2% calcium ascorbate.

In an alternative embodiment, the solution consists of: 95.2% distilled water, 2% citric acid, 2% sodium citrate, 0.2% sodium bisulfite, 0.2% vegetable glycerin, 0.2% potassium sorbate, and 0.2% calcium ascorbate.

The combination of the all natural compounds according to the preferred methods described below preferably results in the solution being substantially transparent, tasteless and odorless.

The advantage of the present solution may be accomplished by the order that the compounds are dissolved in the solution. FIG. 1 illustrates the preferred order of dissolution of the compounds. In each of the below steps, the compounds being added according to the step is preferably dissolved until a clear solution results. Furthermore, the dissolution of the organic compounds is preferably accomplished at or near room temperature.

The first organic compound, potassium sorbate 10, is dissolved in an initial portion of the water until a clear solution results. After a clear solution results, the citric acid 20 is dissolved in the solution until clear. In some embodiments, an intermediate step is conducted between the dissolution of potassium sorbate and the dissolution of the citric acid. The intermediate step is the step of dissolving the calcium ascorbate 15 in the potassium sorbate solution until the solution is again clear.

Next, the sodium citrate is dissolved in the solution until the solution is clear 30. Then, the vegetable glycerin 40 is added to the solution and dissolved until clear.

Subsequently, at least one of: the sea salt 50, the grapefruit seed extract 60, the sodium bisulfite 70, and the decyl glucoside 80 is added to the solution and dissolved until clear.

In some embodiments, the sea salt is added to the solution and dissolved until clear, and then at least one of: sodium bisulfite, decyl glucoside, and grapefruit seed extract is added to the solution and dissolved until clear.

In some embodiments, exactly one of: the sea salt, the sodium bisulfite, the decyl glucoside, and the grapefruit seed extract is added to the solution and dissolved until clear.

In some embodiments, the decyl glucoside may be replaced with cocamidopropyl hydroxysultaine.

Finally, a remaining portion of the water 90 is added to the solution.

In an alternative embodiment, the system comprises a concentrated solution consisting of: 58.5% water, 20% citric acid, 10% sodium citrate, 10% cocamidopropyl hydroxysultaine, 1% glycerin, and 0.5% calcium ascorbate.

According to the present embodiment, the solution is prepared according the following steps:

First, the citric acid is dissolved in substantially all of the water and mixed until a clear solution is produced. Second, the sodium citrate is added to the solution and mixed until the solution is again clear. Third, the cocamidopropyl hydroxysultaine is added to the solution and mixed until the solution is again clear. Finally, the calcium ascorbate is dissolved separately in a remaining portion of the water to form an ancillary solution and the ancillary solution is mixed to the clear solution.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A system for reducing food borne illness comprising:
a solution consisting of: 93.6% triple filtered water or deionized water, 2% citric acid, 2% sodium citrate, 2% sea salt, 0.2% vegetable glycerin and 0.2% potassium sorbate; and
an applicator for applying the solution to a surface of a food substance;
wherein the solution is substantially transparent and odorless.

2. A system for reducing food borne illness comprising:
a solution consisting of: 93.1% triple filtered water or deionized water, 2% citric acid, 2% sodium citrate, 2% sea salt, 0.2% vegetable glycerin, 0.2% potassium sorbate, 0.4% decyl glucoside, and 0.1% calcium ascorbate; and
an applicator for applying the solution to a surface of a food substance;
wherein the solution is substantially transparent and odorless.

3. A system for reducing food borne illness comprising:
a solution consisting of: 95.2% triple filtered water or deionized water, 2% citric acid, 2% sodium citrate, 0.2% sea salt, 0.2% vegetable glycerin, 0.2% potassium sorbate, and 0.2% calcium ascorbate; and
an applicator for applying the solution to a surface of a food substance;
wherein the solution is substantially transparent and odorless.

4. A system for reducing food borne illness comprising:
a solution consisting of: 95% triple filtered water or deionized water, 2% citric acid, 2% sodium citrate, 0.2% sea salt, 0.2% vegetable glycerin, 0.2% potassium sorbate, 0.2% decyl glucoside, and 0.2% calcium ascorbate; and
an applicator for applying the solution to a surface of a food substance;
wherein the solution is substantially transparent and odorless.

5. A system for reducing food borne illness comprising:
a solution consisting of: 95.2% triple filtered water or deionized water, 2% citric acid, 2% sodium citrate, 0.2% grapefruit seed extract, 0.2% vegetable glycerin, 0.2% potassium sorbate, and 0.2% calcium ascorbate; and
an applicator for applying the solution to a surface of a food substance;
wherein the solution is substantially transparent and odorless.

6. A system for reducing food borne illness comprising:
a solution consisting of: 95.2% triple filtered water or deionized water, 2% citric acid, 2% sodium citrate, 0.2% sodium bisulfite, 0.2% vegetable glycerin, 0.2% potassium sorbate, and 0.2% calcium ascorbate; and
an applicator for applying the solution to a surface of a food substance;
wherein the solution is substantially transparent and odorless.

7. The system of claim 1, wherein the application comprises at least one of a towelette and a spray bottle.

8. The system of claim 2, wherein the application comprises at least one of: a towelette and a spray bottle.

9. The system of claim 3, wherein the application comprises at least one of: a towelette and a spray bottle.

10. The system of claim 4, wherein the application comprises at least one of: a towelette and a spray bottle.

11. The system of claim 5, wherein the application comprises at least one of: a towelette and a spray bottle.

12. The system of claim 6, wherein the application comprises at least one of: a towelette and a spray bottle.

* * * * *